United States Patent [19]
Joustra

[11] Patent Number: 5,886,253
[45] Date of Patent: Mar. 23, 1999

[54] PENETROMETER

[75] Inventor: Kornelis Joustra, Leidschendam, Netherlands

[73] Assignee: Verenigde Bedrijven Van den Berg Heerenveen Holding B.V., Netherlands

[21] Appl. No.: 88,632

[22] Filed: Jun. 2, 1998

[30] Foreign Application Priority Data

Jun. 4, 1997 [NL] Netherlands ............................ 1006228

[51] Int. Cl.$^6$ ..................................................... G01N 3/00
[52] U.S. Cl. ....................................................... 73/84
[58] Field of Search ..................... 73/9, 84, 784

[56] References Cited

U.S. PATENT DOCUMENTS 5,042,595  8/1991  Ladanyi ....................................... 73/84

FOREIGN PATENT DOCUMENTS 369464  2/1973  U.S.S.R. ..................................... 73/84
1191521  11/1985  U.S.S.R. ..................................... 73/84

*Primary Examiner*—Robert Raevis
*Attorney, Agent, or Firm*—Ladas & Parry

[57] ABSTRACT

Penetrometer comprising a probe with a conical nose, a cylindrical friction casing, and means for measuring axial friction forces acting on the friction casing when the probe is advanced in an area of ground which is to be analysed.

The probe furthermore has a conical casing and means for measuring the axial forces acting on the conical casing.

The conicity of the conical casing is so minor that the conical casing causes a displacement of the surrounding ground which is directed substantially transverse to the axial direction of the probe.

8 Claims, 1 Drawing Sheet

U.S. Patent     Mar. 23, 1999     5,886,253 ject of the present invention is to provide a
PENETROMETER

BACKGROUND OF THE INVENTION

The present invention relates to a penetrometer comprising a probe with a conical nose, a cylindrical friction casing, and means for measuring axial friction forces acting on the friction casing when the probe is advanced in an area of ground which is to be analysed.

A penetrometer of this kind is known, for example, from EP 0 010 988. In this document, the penetrometer is provided with a first force transducer for measuring the forces acting on the conical nose, which is referred to below as the cone, and with a second force transducer for measuring the friction forces acting axially on the cylindrical friction casing. When the known penetrometer is pressed vertically into the ground at a substantially constant speed, the cone resistance and the friction force are measured simultaneously. As a result, a soil profile is obtained, which is desirable, for example, for designing the foundations of a building.

In order to determine the soil profile, it is also desirable to gain an insight into the horizontal strength of the ground. A generally known device for determining the horizontal strength of the ground was developed by Prof. S. Marchetti and is known as the "Marchetti Dilatometer". The drawback of this known device is that the horizontal strength of the ground can only be measured while the instrument is standing still, with the result that, in order to determine a soil profile, the device has to be pressed into the ground in steps, for example of 0.2 meter, in order in this way to obtain a sufficiently high number of measured values. For this reason, this measurement method is time-consuming. Furthermore, to determine the soil profile it is sometimes also necessary to carry out penetrometer tests.

The Cambridge Institute has developed a probe, under the name of "Cone Pressuremeter" which comprises a conventional penetrometer with a conical nose and a friction casing, on the one hand, and a pressure-measuring apparatus which is arranged one meter from the conical nose, on the other hand. The pressure-measuring apparatus comprises a diaphragm, the diameter of which can be expanded by the application of internal pressure. This "Cone Pressuremeter" is pressed into the ground in steps, in order to expand the diaphragm while the device is at a standstill, then to carry out the measurement, and finally to allow the diaphragm to deflate again, after which the probe is pressed further into the ground.

The Russian publication SU-A-548,684, published on 22 Mar. 1977, discloses a penetrometer which is designed to simultaneously determine both the cone resistance, the friction forces and the horizontal ground pressure. This known penetrometer has a cone with an associated first force transducer for measuring the cone resistance. Furthermore, this known penetrometer has a substantially cylindrical metal casing which is cut open in the axial direction. As a result, the diameter of the casing can vary under the effect of radial forces exerted by the ground. The known penetrometer is provided with a second force transducer for measuring the forces acting on the casing in the axial direction and with means for measuring the change in diameter of the casing, which change provides an insight into the horizontal pressure exerted on the casing by the ground. This known penetrometer has the advantage over the Marchetti Dilatometer that the three measurements are performed simultaneously and there is no need to move the penetrometer in steps.

The split-casing design of the penetrometer which is known from SU-A-548,684 has the drawback that it is not possible to interpret the measurement results unambiguously. As the horizontal pressure on the casing increases, the diameter of the casing will decrease. This results in an active stress condition in the ground which is characterized by a fall in the horizontal pressures as a result of the arch action in the surrounding ground. This fall depends on the frictional properties of the material of which the ground is composed. An increase in the diameter of the casing of the known penetrometer causes a passive stress condition in the ground, with the result that the horizontal pressures in the ground actually increase. As the penetrometer is pressed into the ground, the variations in the composition of the ground which arrive as the depth increases will cause the stress condition to vary constantly between passive and active, with the result that the measurement results obtained using the penetrometer cannot be interpreted unambiguously. A further drawback of this known penetrometer is that its operation can be interfered with by the penetration of groundwater and soil material.

SUMMARY OF THE INVENTION

The object of the present invention is to provide a penetrometer which eliminates the abovementioned drawbacks.

This object is achieved by means of a penetrometer in accordance with the preamble of claim 1 which is characterized in that the probe furthermore comprises a conical casing and means for measuring the axial forces acting on the conical casing.

The conical casing causes a substantially horizontal expansion of the space formed by the probe in the ground. The resistance of the ground to this expansion provides a defined force which acts perpendicularly on the conical casing. The cylindrical friction casing does not cause any horizontal expansion of the ground. By then measuring both the axial force on the cylindrical friction casing and the axial force on the conical casing and comparing the two measurement values with one another, it is possible to obtain an insight into the resistance of the ground to the horizontal expansion caused by the conical casing.

Further advantageous embodiments of the penetrometer according to the invention are described in the sub-claims and the following description with reference to the drawing, in which:

DETAILED DESCRIPTION OF THE PREFERRED EMBODIMENTS

Figures 1, 2:
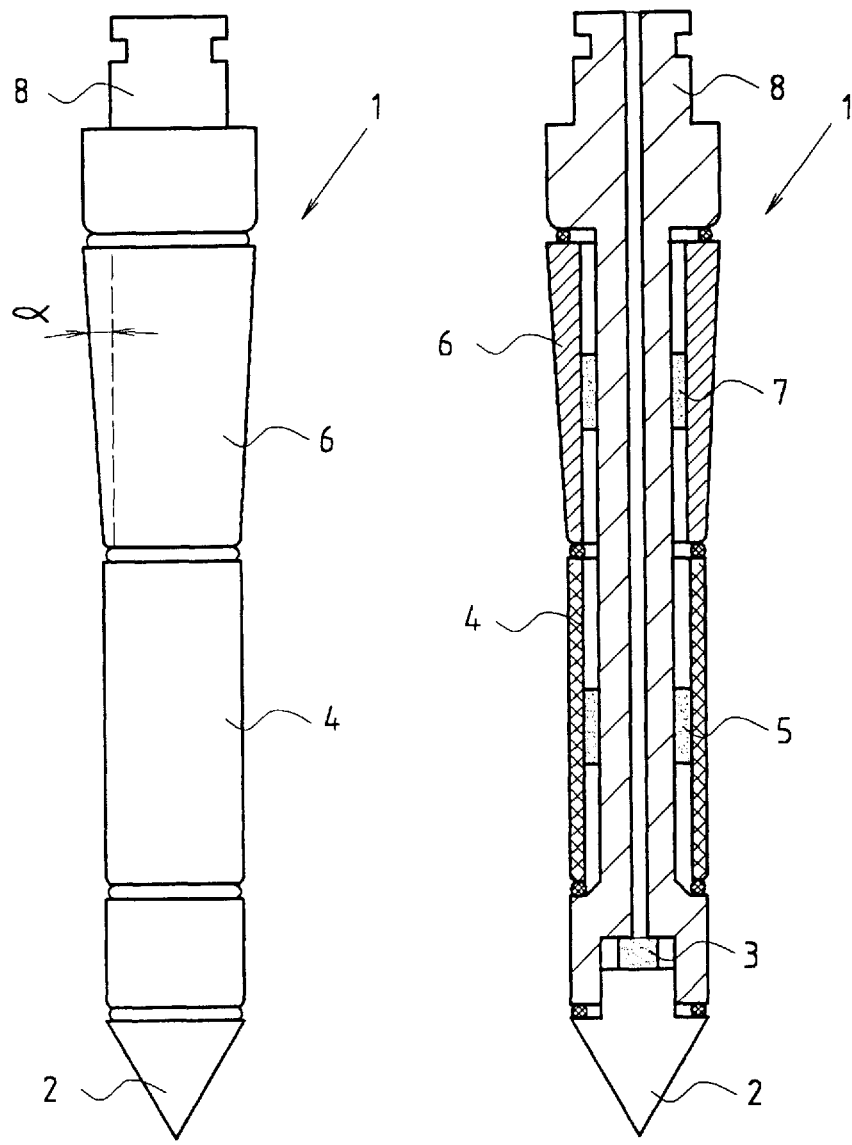
FIG. 1 shows a side view of a preferred embodiment of the penetrometer according to the invention, and FIG. 2 diagrammatically shows a longitudinal section through the penetrometer in accordance with FIG. 1.

FIG. 1 shows a preferred embodiment of the probe 1 of the penetrometer according to the invention.

The probe 1 has an elongate body with a conical nose 2, referred to below as the cone and has a generally known cone angle of 60°, at that end of the body which is to be pressed into the ground. As can be seen in FIG. 2, first force transducer means 3 are provided, which measure the axial forces acting on the cone 2, which are generally referred to by the term cone resistance.

At an axial distance from the cone 2, the probe 1 has a friction casing 4. The friction casing 4 is cylindrical with a constant diameter over its entire axial length. The friction casing 4 can be moved axially to a slight extent with respect to the body of the probe 1, and second force transducer means 5, with which the friction forces acting on the friction casing 4 can be measured, are placed between the friction casing 4 and the body of the probe 1.

The friction casing 4 is situated in a known manner behind the cone 2, with the result that the measurement of the friction force carried out using the penetrometer according to the invention is comparable to the measurement carried out using a conventional penetrometer.

On that side of the friction casing 4 which is remote from the cone 2, the probe 1 is provided with a conical casing 6. On the side of the friction casing 4, the conical casing 6 has a diameter which is equal to that of the friction casing 4. In the direction away from the friction casing 4, the diameter of the conical casing 6 increases gradually. The conical casing 6 is designed in such a manner that it is not deformed significantly under the influence of the radial forces exerted on it by the ground. The conical casing 6 can be moved axially to a slight extent with respect to the body of the probe 1, and third force transducer means 7 are provided for measuring the axial forces on the conical casing 6.

The conicity of the conical casing 6 is low, in order to ensure that the ground is pressed away by the conical casing 6 transversely to the penetration direction of the probe 1, corresponding to the longitudinal axis of the probe 1. In FIGS. 1 and 2, the conicity of the conical casing 6 is exaggerated for the sake of clarity of the illustration. Preferably, the angle a between the outer surface of the conical casing 6 and the longitudinal axis of the probe 1 is less than 3°. In an embodiment which is advantageous in practice, this angle is 1.3°.

Advantageously, the outer surface area of the conical casing 6 is substantially the same size as the surface area of the friction casing 4.

To determine a soil profile, the probe 1 is pressed vertically into the ground at a substantially constant speed with the aid of a bar which is coupled to the head 8 of the probe 1. The first force transducer means 3 show the level of the cone resistance. The second force transducer means 5 show the friction force on the friction casing 4. The third force transducer means 7 show the axial force on the conical casing 6. Owing to the low level of conicity of the conical casing 6, this axial force is caused substantially by friction. Since the conical casing 6 presses the ground away to the sides, the friction force on the conical casing 6 will be greater than the friction force on the friction casing 4. The difference between the force measured by the second force transducer means 5 and the force measured by the third force transducer means 7 is dependent on the horizontal strength of the ground under the ground stresses occurring. The penetrometer 1 therefore simultaneously measures the cone resistance and the friction force, providing an indication of the horizontal strength of the ground.

The theory of the expansion of a cylindrical space in an elasto-plastic material allows a quantitative calculation of the modulus of elasticity of the ground in the horizontal direction.

In an embodiment which is not shown, the friction casing 4 may be disposed at a greater distance from the cone 2, in order to reduce any interfering effects of the cone 2 on the ground.

In another variant which is not shown of the probe illustrated in the drawing, there may be provision for an additional friction casing to be disposed between the above-described friction casing 4 and the cone 2. In this case, that part of this probe which comprises the cone and the additional friction casing is preferably of identical design to a generally known probe, so that the measurement results of the probe according to the invention can be directly compared to those obtained with the known probe, and the friction casing 4 is used to calculate the measurement results obtained with the conical casing 6 disposed behind it.

What is claimed is:

1. Penetrometer comprising a probe with a conical nose, a cylindrical friction casing, and means for measuring axial friction forces acting on the friction casing when the probe is advanced in an area of ground which is to be analysed, wherein the probe furthermore comprises a conical casing and means for measuring the axial forces acting on the conical casing.

2. Penetrometer according to claim 1, in which the conicity of the conical casing is so minor that the conical casing causes a displacement of the surrounding ground which is directed substantially transverse to the axial direction of the probe.

3. Penetrometer according to claim 2, in which the conicity of the conical casing is less than 3°.

4. Penetrometer according to claim 1, in which the conical casing is disposed on that side of the friction casing which is remote from the nose.

5. Penetrometer according to claim 1, in which the conical casing has a diameter at one of its axial ends which corresponds to the diameter of the friction casing.

6. Penetrometer according to claim 1, in which the surface area of the conical casing is substantially equal to the surface area of the friction casing.

7. Penetrometer according to claim 1, in which two cylindrical friction casings are disposed between the conical nose and the conical casing, and in which means are provided for each of these friction casings for measuring axial friction forces acting on the friction casing in question when the probe is advanced in an area of ground to be analysed.

8. Penetrometer according to claim 1, in which calculation means are provided which determine the modulus of elasticity in the horizontal direction of the ground.

* * * * *